US012714854B2

(12) United States Patent
Tucker

(10) Patent No.: US 12,714,854 B2
(45) Date of Patent: Aug. 25, 2026

(54) WEARABLE EEG/EIT SYSTEM FOR MONITORING AND ENHANCING GLYMPHATIC CLEARANCE (GC) DURING SLEEP USING SKIN-PATH-CORRECTED SINGLE-FREQUENCY IMPEDANCE TO COMPUTE A GC INDEX WITH GC-WINDOW-GATED STIMULATION

(71) Applicant: Brain Electrophysiology Laboratory Company, LLC, Eugene, OR (US)

(72) Inventor: Don M. Tucker, Eugene, OR (US)

(*) Notice: Subject to any disclaimer, the term of this patent is extended or adjusted under 35 U.S.C. 154(b) by 0 days.

(21) Appl. No.: 19/350,041

(22) Filed: Oct. 5, 2025

(65) Prior Publication Data

US 2026/0027364 A1 Jan. 29, 2026

(51) Int. Cl.
*A61B 5/00* (2006.01)
*A61N 1/36* (2006.01)

(52) U.S. Cl.
CPC ........ *A61N 1/36031* (2017.08); *A61B 5/4088* (2013.01); *A61B 5/7275* (2013.01); *A61N 1/36025* (2013.01); *A61N 1/36034* (2017.08)

(58) Field of Classification Search
CPC ............ A61N 1/36031; A61N 1/36025; A61N 1/36034; A61B 5/4088; A61B 5/7275
See application file for complete search history.

(56) References Cited

U.S. PATENT DOCUMENTS

2024/0130680 A1* 4/2024 Dagum ................ A61B 5/6814
2025/0144427 A1* 5/2025 Worrell .................. A61B 5/053

* cited by examiner

*Primary Examiner* — John R Downey

(57) ABSTRACT

A system for electrical stimulation and recovery of impressed currents during sleep to measure the electrical impedance of intracranial tissue through a single-frequency current stimulation, and decrease the brain impedance through other stimulation parameters, thereby increasing extracellular space and improving glymphatic flow (as indexed dynamically by the concurrent brain impedance measure). A skin-path-correction factor is estimated to allow the subtraction of the electrode-to-skin impedance and thereby estimate the brain impedance compartment separately. Based on computational modeling of electrical conductivity of head tissues, the electrodes are placed at forehead and nuchal sites to optimize current flow through high-conductive skull orifices. Current flow estimation is monitored at the critical orifice of the foramen magnum, and safety limits are monitored and enforced for individual electrodes and for key brain structures.

20 Claims, 3 Drawing Sheets

WEARABLE EEG/EIT SYSTEM FOR MONITORING AND ENHANCING GLYMPHATIC CLEARANCE (GC) DURING SLEEP USING SKIN-PATH-CORRECTED SINGLE-FREQUENCY IMPEDANCE TO COMPUTE A GC INDEX WITH GC-WINDOW-GATED STIMULATION

FIELD

The disclosure relates to wearable neuromonitoring and neuromodulation. In particular, it concerns integrated electroencephalography (EEG) and electrical impedance tomography/spectroscopy (EIT/EIS) to monitor cerebrospinal fluid-interstitial fluid exchange and to enhance glymphatic clearance during sleep, using single-frequency impedance with skin-path correction and window-gated transcranial electrical stimulation (tES).

BACKGROUND

Extracellular space (ECS) fraction and fluid content modulate low-frequency tissue conductivity, and they also determine clearance of waste metabolites from the brain Glymphatic Clearance (GC). Wearable systems that sample a single-frequency intracranial impedance signal during sleep offer a practical proxy for ECS dynamics but are confounded by high and variable skin-electrode impedances. A need remains for an integrated EEG/EIT approach that (i) estimates an intracranial impedance component while correcting skin-path contributions; (ii) fuses the impedance signal with sleep stage to identify glymphatic-favorable windows; and (iii) optionally delivers tES within those windows under anatomical current-routing and safety constraints.

STATEMENT REGARDING PRIOR ART

References such as WO 2018/039602 A1, U.S. Pat. No. 11,426,577 B2, and U.S. Pat. No. 12,005,251 B2 disclose head-mounted stimulation using burst patterns in which rest intervals exceed stimulation intervals with vascular/BOLD alternation endpoints. The present disclosure differs by (i) quantifying foramen-magnum routing via FM-COI; (ii) using continuous or symmetric-duty stimulation with quiescent or rest intervals not exceeding stimulus block duration; (iii) continuously or regularly acquiring a single-frequency intracranial impedance signal and combining it with Convolutional Neural Net (CNN) sleep staging to detect GC window and optimize stimulation while preserving sleep architecture.

SUMMARY

In one aspect, a wearable device places an active stimulation electrode at a suboccipital site and a return electrode on the forehead to bias current into the posterior fossa. An EEG front end electronics and a single-frequency impedance front end (e.g., ~7-8 Hz, nanoamp AC injection) operate continuously or at regular intervals during sleep. One or more processors obtain a head model to compute a Foramen-Magnum Current-Occupancy Index (FM-COI) and enforce field/skin safety caps; classify sleep with a convolutional neural network (CNN); compute a Global and/or Regional Glymphatic-Clearance Index (GCI/RGCI) from an intracranial-impedance/ECS estimate that is explicitly corrected for skin paths; detect glymphatic-clearance (GC) windows (increased ECS, decreased impedance); and schedule stimulation within GC windows while preserving sleep architecture.

Skin-path-corrected intracranial impedance (SPC-Z) may be estimated from electrode pairs that traverse brain tissue by subtracting a weighted combination of nearby "skin-only" control pairs (e.g., same-side frontal-mastoid and mastoid-mastoid) and/or by regression, adaptive filtering, or model-based inversion. Stage-conditioned and subject-specific parameters (weights, priors) can be learned from historical nights.

Definitions

- Single-frequency EIT channel: An impedance acquisition at a single frequency (such as ~7-8 Hz) using low-amplitude AC injection (such as nanoamperes), operated continuously or intermittently during sleep.
- SPC-Z: Skin-path-corrected intracranial impedance: an estimate of intracranial impedance derived by suppressing electrode-gel-skin and scalp conduction contributions using control pairs and/or model-based terms.
- GCI/RGCI: Global/Regional Glymphatic-Clearance Index: a scalar or vector metric computed from SPC-Z and regional sensitivities/priors (due to regional head tissue conductivity), summarizing clearance propensity across the night or within GC windows.
- GC window: A time window predicted from sleep stage and SPC-Z signatures to favor CSF-ISF exchange and clearance.
- FM-COI: Foramen-Magnum Current-Occupancy Index: a model-based ratio quantifying the fraction of injected current routed through a foramen-magnum region of interest.
- Sleep-architecture safety: Constraints to preserve sleep structure (e.g., a REM, Rapid Eye Movement sleep, floor and limits on N3, deep Non-REM stage 3, fragmentation) in addition to electrical safety caps.

DETAILED DESCRIPTION

System Overview

Figure 1:
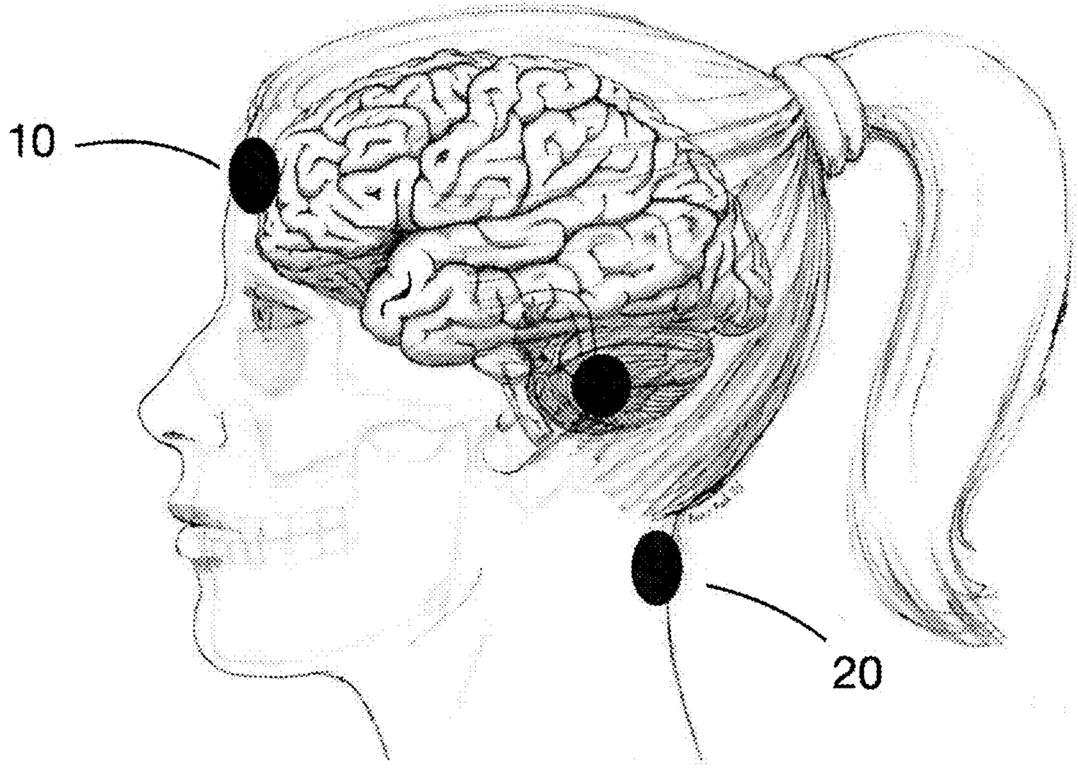
FIG. 1: Example position of tES/EEG/EIT electrodes in relation to head and skull anatomy. 10: Forehead electrode. 20: Nuchal (suboccipital) electrode.
Figure 2:
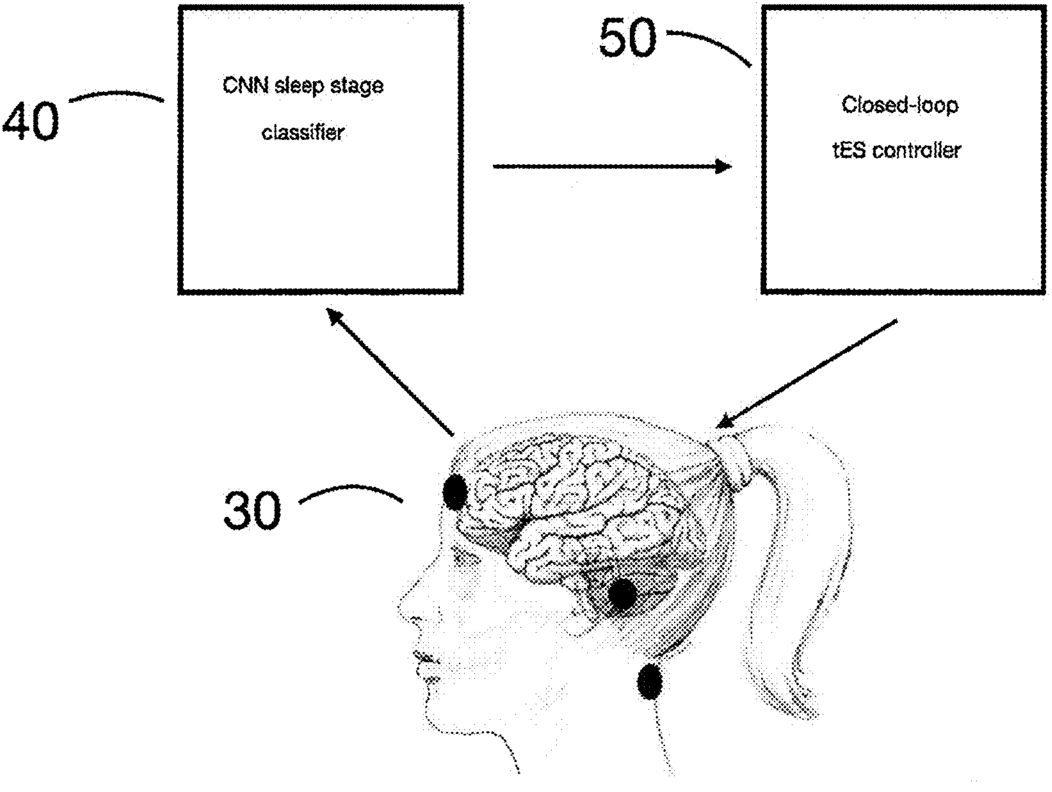
FIG. 2: Relationship of major system components. 30: Electrode positions as placed by a headband for EEG/tES/EIT. 40: Convolutional Neural Net machine learning operating on EEG to classify neurophysiological sleep stages. 50: Closed-loop controller for staging tES optimally in relation to sleep stages.
Figure 3:
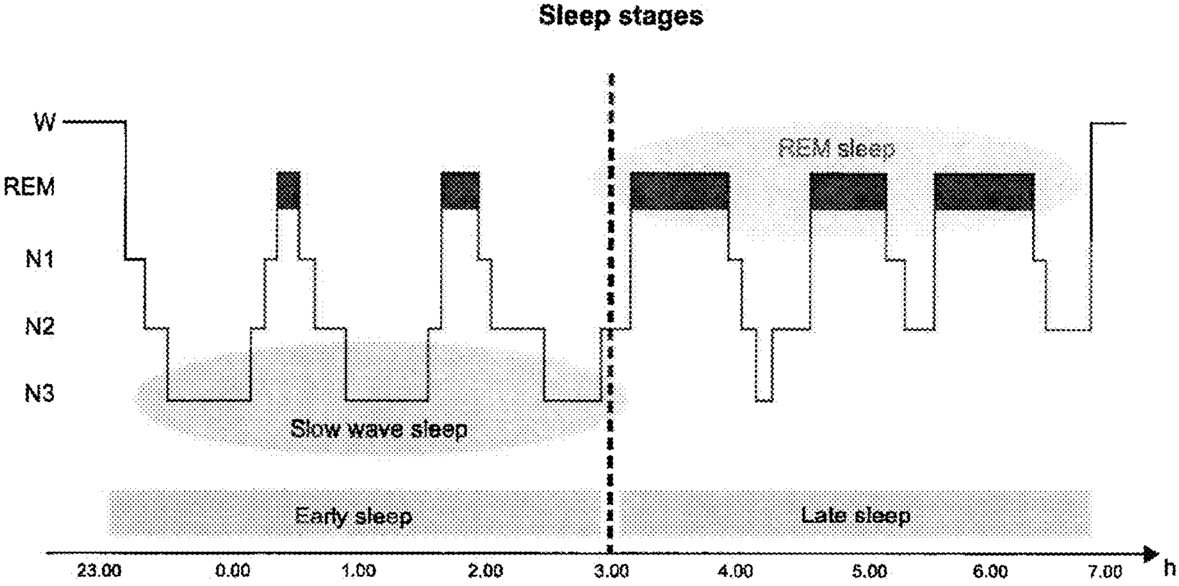
FIG. 3: Illustration of typical sleep stages in a chart described as a hypnogram, including wake (W), Rapid Eye Movement sleep (REM), Non-REM stage 1 (N1), Non-REM stage 2 (N2), and Non-REM stage 3 (N3). The early night is dominated by Non-REM and the later night by REM.

A flexible wearable with a suboccipital (nuchal) electrode contact for tES current delivery and a forehead return. The controller hosts EEG, a single-frequency impedance channel, and a stimulation front end capable of continuous or symmetric-duty waveforms (e.g., 0.1-2 Hz slow-oscillation tES). The impedance channel runs continuously or at scheduled intervals to produce an impedance time series synchronized with EEG (electroencephalography).

Skin-Path Correction (SPC-Z)

The electrode-skin interface is a source of impedance that must be removed to estimate brain impedance (Z) correctly. To estimate Skin-Path Corrected brain impedance, SPC-Z, the processor forms brain-inclusive paths (e.g., forehead→contralateral mastoid; midline→mastoid) and suppresses skin contributions using proximal control pairs (e.g., forehead→forehead; mastoid→mastoid; same-side forehead→mastoid). One implementation subtracts half the sum of two nearest skin controls from a brain-inclusive path. More generally, a parametric form $\hat{Z}$_brain=Z_meas−α·Z_skin1−β·Z_skin2−γ·Z_skin3 is fit by ridge regression or adaptive filtering, optionally stage-conditioned and subject-specific. The processor rejects poor-quality epochs (motion, low SNR), optionally removes a slow time-of-night drift, and produces SPC-Z features (level, slope, variance, stage-conditioned contrasts).

GCI/RGCI Computation

Regional sensitivity maps from a subject-specific or atlas-based head model transform SPC-Z to compartment-level estimates (cortex, deep gray, cerebellum, cisterna magna, upper spinal subarachnoid space) where extracellular space (ECS) is known to be indexed by brain electrical impedance. GCI may be the volume-weighted sum of RGCI or a principal-component projection. GC windows are detected from stage labels and SPC-Z features; stimulation is gated to the windows while preserving sleep-architecture safety and electrical caps (hindbrain E-field, cranial-nerve exposure, skin current-density).

Use Cases

1) Nightly monitoring: compute GCI/RGCI trajectories to assess clearance propensity across the night, including stage-specific minima and overnight slopes. 2) Closed-loop enhancement: schedule slow-oscillation tES during GC windows to optimize RGCI while preserving REM and N3 continuity. 3) Longitudinal risk scoring: aggregate nightly GCI/RGCI features to predict chronic impairment of clearance and stratify risk for cognitive decline.

Examples

Example A—Skin-path-corrected impedance from Sleep WISP (Wireless Interface Sensor Pod; neurosom.net) montage: Using forehead (Fp1, Fp2), mastoids (M1, M2), and a midline common (COM), compute SPC-Z for Fp2→M1 as $\hat{Z}$_brain=|Fp2−M1|−½(|Fp2−Fp1|+|M1−M2|). Other brain-inclusive paths (Fp1→M2, COM→M1) are similarly corrected.

Example B— WISP with continuous impedance: Five× 4-min 0.75 Hz blocks with quiescent intervals≤the immediately preceding block; compute RGCI in real time; preserve REM minutes above a floor, titrate amplitude within anatomical and electrical caps.

Example C—Training and calibration: Intermittent multi-frequency EIS with EEG blanking validates single-frequency mappings via Kramers-Kronig consistency and joint inversion; cohort archives (e.g., hdEEG/EIT) provide priors for impedance-to-compartment mappings and GC-window definitions.

The invention claimed is:

1. A wearable neuromonitoring and neuromodulation system comprising: (a) an active stimulation electrode configured for placement at at least one suboccipital (nuchal) skin site and a return electrode configured for placement on a subject's forehead; (b) an EEG front end and an impedance front end configured to acquire a single-frequency intracranial impedance signal at a frequency of about 7-8 Hz using low-amplitude AC injection; and (c) one or more processors configured to: (i) obtain a head conductivity model; (ii) compute a Foramen-Magnum Current-Occupancy Index (FM-COI) and enforce electrical and sleep-architecture safety limits; (iii) classify sleep stage using a convolutional neural network (CNN); (iv) compute a skin-path-corrected intracranial impedance (SPC-Z) from the single-frequency signal; (v) from SPC-Z and regional sensitivities, estimate a Global and/or Regional Glymphatic-Clearance Index (GCI/RGCI); and (vi) deliver continuous or symmetric-duty transcranial electrical stimulation during GC windows identified from (iii)-(v) to optimize GCI/RGCI while maintaining the safety limits.

2. The system of claim 1, wherein SPC-Z for a brain-inclusive path is computed by subtracting half the sum of two nearest skin-only control pairs from the measured path.

3. The system of claim 1, wherein SPC-Z is computed by fitting $\hat{Z}$_brain=Z_meas−α·Z_skin1−β·Z_skin2−γ·Z_skin3 with α, β, and γ determined by stage-conditioned ridge regression or adaptive filtering using historical and/or same-night data.

4. The system of claim 1, wherein skin-only control pairs comprise at least one of: forehead-forehead, mastoid-mastoid, and same-side forehead-mastoid electrode pairs.

5. The system of claim 1, wherein at least one of the one or more processors performs artifact rejection and quality gating that excludes impedance epochs with excessive motion, low signal-to-noise ratio, or inconsistent phase.

6. The system of claim 1, wherein at least one of the one or more processors removes a slow time-of-night drift from SPC-Z prior to GC-window detection or GCI/RGCI computation.

7. The system of claim 1, wherein GCI is computed as a volume-weighted sum or principal-component projection of RGCI over multiple regions of interest.

8. The system of claim 1, wherein sleep-architecture safety comprises preserving REM minutes above a subject-specific floor and limiting N3 fragmentation.

9. The system of claim 1, wherein the single-frequency impedance injection amplitude is in the nanoampere range and the acquisition bandwidth is configured to minimize interaction with the stimulation waveform.

10. The system of claim 1, wherein at least one of the one or more processors performs intermittent multi-frequency EIS with EEG blanking to validate single-frequency mappings via Kramers-Kronig consistency and joint inversion.

11. The system of claim 1, wherein FM-COI is at least 0.20 at 1 mA RMS and hindbrain and cranial-nerve electric-field caps are maintained at ≤0.5 V/m RMS and ≤0.2 V/m RMS, respectively.

12. The system of claim 1, wherein an atlas-based model is scaled by head anthropometrics and calibrated by impedance-transfer measurements to estimate FM-COI and regional sensitivities without subject-specific imaging.

13. A method comprising: placing an active electrode at a suboccipital (nuchal) site and a return electrode on a subject's forehead; computing FM-COI from a head model and enforcing field and skin current-density caps and sleep-architecture constraints; continuously or regularly acquiring a single-frequency impedance signal during sleep at a frequency of about 7-8 Hz; classifying sleep stage with a CNN; computing SPC-Z by skin-path correction by fitting $\hat{Z}$_brain=Z_meas−a·Z_skin1−β·Z_skin2−γ·Z_skin3; estimating GCI/RGCI from SPC-Z; and delivering transcranial electrical stimulation during GC windows to optimize GCI/RGCI while maintaining the constraints.

14. The method of claim 13, wherein GC windows are defined by N3 epochs with SPC-Z features exceeding a stage-conditioned threshold learned from historical data.

15. The method of claim 13, wherein stimulation comprises a 0.75 Hz slow-oscillation protocol in blocks with ramps and quiescent intervals not exceeding the immediately preceding block.

16. The method of claim 13, further comprising respiratory and/or cardiac phase-locking of stimulation to maximize a cranio-cervical outflow or GCI/RGCI objective.

17. The method of claim 13, further comprising rejecting impedance epochs with excessive motion or poor quality and re-acquiring during the next valid window before updating GCI/RGCI or stimulation parameters.

18. The method of claim 13, wherein SPC-Z is computed using a subtraction model that subtracts half the sum of two nearest skin-only control pairs from a brain-inclusive path.

19. The method of claim 13, wherein SPC-Z is computed using a regression model with adaptive weights for skin-only control pairs, estimated per stage or per subject.

20. A non-transitory computer-readable medium storing instructions that, when executed, cause one or more processors to: obtain a head conductivity model; compute a Foramen-Magnum Current-Occupancy Index (FM-COI) and enforce electrical and sleep-architecture safety limits; classify sleep stage using a convolutional neural network (CNN); compute a skin-path-corrected intracranial impedance (SPC-Z); estimate GCI/RGCI from SPC-Z and regional sensitivities; identify GC windows from the classified sleep stage and SPC-Z; and schedule delivery of transcranial electrical stimulation during the GC windows while maintaining the safety limits.

* * * * *